(12) United States Patent
Sawan et al.

(10) Patent No.: US 12,203,909 B2
(45) Date of Patent: Jan. 21, 2025

(54) COMPOSITIONS FOR CONJUGATING A SULFONEPHTHALEIN DYE TO A SUBSTRATE

(71) Applicant: WATERGURU, INC., San Francisco, CA (US)

(72) Inventors: Samuel P. Sawan, San Rafael, CA (US); Alexander V. Yurkovetskiy, Littleton, MA (US)

(73) Assignee: WaterGuru, Inc., San Francisco, CA (US)

( * ) Notice: Subject to any disclaimer, the term of this patent is extended or adjusted under 35 U.S.C. 154(b) by 373 days.

(21) Appl. No.: 17/326,580

(22) Filed: May 21, 2021

(65) Prior Publication Data

US 2021/0349064 A1    Nov. 11, 2021

Related U.S. Application Data

(63) Continuation of application No. PCT/US2019/063532, filed on Nov. 27, 2019.

(60) Provisional application No. 62/771,860, filed on Nov. 27, 2018.

(51) Int. Cl.
| | |
|---|---|
| *C09B 11/08* | (2006.01) |
| *G01N 31/22* | (2006.01) |
| *G01N 33/18* | (2006.01) |

(52) U.S. Cl.
CPC ............ *G01N 31/221* (2013.01); *C09B 11/08* (2013.01); *G01N 33/18* (2013.01)

(58) Field of Classification Search
CPC ....................................................... C09B 11/08
See application file for complete search history.

(56) References Cited

U.S. PATENT DOCUMENTS

| | | | | |
|---|---|---|---|---|
| 2,745,720 A | * | 5/1956 | Schwarzenbach | ...... C09B 11/08 436/163 |
| 2,980,696 A | * | 4/1961 | Koerbl | ..................... C09B 11/08 436/83 |
| 3,301,870 A | * | 1/1967 | Terzijska | ................ C09B 11/08 436/79 |
| 4,287,153 A | | 9/1981 | Towsend | |
| 2007/0154621 A1 | | 7/2007 | Raad | |
| 2009/0024096 A1 | | 1/2009 | Hai et al. | |
| 2019/0032277 A1 | * | 1/2019 | Hoogenboom | ........... D06P 3/66 |

* cited by examiner

*Primary Examiner* — Jennifer Wecker
*Assistant Examiner* — Michelle Adams
(74) *Attorney, Agent, or Firm* — Elmore Patent Law Group, P.C.; Edgar W. Harlan; Carolyn S. Elmore

(57) ABSTRACT

The present invention provides derivatized indicator compounds, such as pH indicator compounds, which can be covalently immobilized to a variety of solid substrates to produce an indicator pad. Such pads can be used to monitor water quality in variety of settings. In particular, the pads of the invention are useful in devices which monitor the quality of recreational water, such as water in swimming pools, hot tubs, and amusement park attractions, including water slides, and water-based rides. The present invention overcomes the limitations of commercially available pad chemistries.

3 Claims, 9 Drawing Sheets

COMPOSITIONS FOR CONJUGATING A SULFONEPHTHALEIN DYE TO A SUBSTRATE

RELATED APPLICATIONS

This application is a continuation of International Application No. PCT/US2019/063532, which designated the United States and was filed on Nov. 27, 2019, published in English, which claims the benefit of U.S. Provisional Application No. 62/771,860, filed on Nov. 27, 2018. The entire teachings of the above applications are incorporated herein by reference.

BACKGROUND OF THE INVENTION

There are a number of commercially available water testing pads or strips used to test a wide variety of recreational water chemistries. Commercial water testing pads or strips are typically prepared by adsorbing an indicator dye onto an absorbent material such as cellulose. A typical commercial test pad is meant to be briefly dipped into the water to be tested and withdrawn immediately. The color that develops on the pad is meant to be read after a specific number of seconds after immersion in the water. The color is compared to a standard color testing chart to determine the chemical property specified for that pad.

Adsorbed dyes can readily desorb from the pad if left immersed for too long. Further, pads that are not read within the defined period of time yield inaccurate results for the property being measured. Additionally, it has been found that such pads are sensitive to their storage condition. For example, pads that are exposed to humidity adsorb water which results in a significant change in the pads response to the analyte in question. For such reasons, commercially produced pads for the determination of water chemistry levels have been found to be inadequate for any device that needs to store weeks or months' worth of pads in proximity to the recreational water source for subsequent measurement.

An automated water testing and treatment device that uses photometric readings of pad chemistry to monitor the water quality must store a large number of pads in the device for future use. If the pads are stored in barrier films, testing has shown that significant degradation of the pad chemistry can occur with absorption of even small amounts of water over time. Further color changes may also occur resulting in inaccurate readings of water chemistry values such as pH or free chlorine.

There is a need for improved indicator pads that overcome the disadvantages of currently available commercial pads that also have a response which is suitable for monitoring the quality of recreational water, such as water in swimming pools and hot tubs, using spectrophotometric techniques such as reflectance or absorbance.

SUMMARY OF THE INVENTION

The present invention provides derivatized indicator compounds, such as pH indicator compounds, which can be covalently immobilized to a variety of solid substrates to produce an indicator pad. Such pads can be used to monitor water quality in variety of settings. In particular, the pads of the invention are useful in devices which monitor the quality of recreational water, such as water in swimming pools, hot tubs, and amusement park attractions, including water slides, and water-based rides. The present invention overcomes the limitations of commercially available pad chemistries.

In one embodiment, the invention provides a method for preparing a reactive derivative of a phenolic indicator dye which reacts with a variety of solid substrates resulting in covalent attachment of the phenolic indicator dye to the surface of the substrate. Preferably, the reactive derivative is produced by a method comprising reacting the phenolic indicator dye with formaldehyde or paraformaldehyde. The resulting reactive derivative is then contacted with a solid substrate under conditions sufficient for covalent conjugation of the reactive derivative to the surface of the substrate, thereby forming a dye-conjugated substrate.

In another embodiment, the invention provides a reactive derivative of a phenolic dye prepared as described herein.

In another embodiment, the invention provides a dye-derivatized substrate which can be prepared by the methods disclosed herein.

In another embodiment, the invention provides an indicator pad comprising a dye derivatized substrate as described herein.

In a further embodiment, the invention provides methods of using a dye-derivatized substrate or indicator pad of the invention for monitoring one or more characteristics of water, such as recreational water.

DETAILED DESCRIPTION OF THE INVENTION

Figure 1:
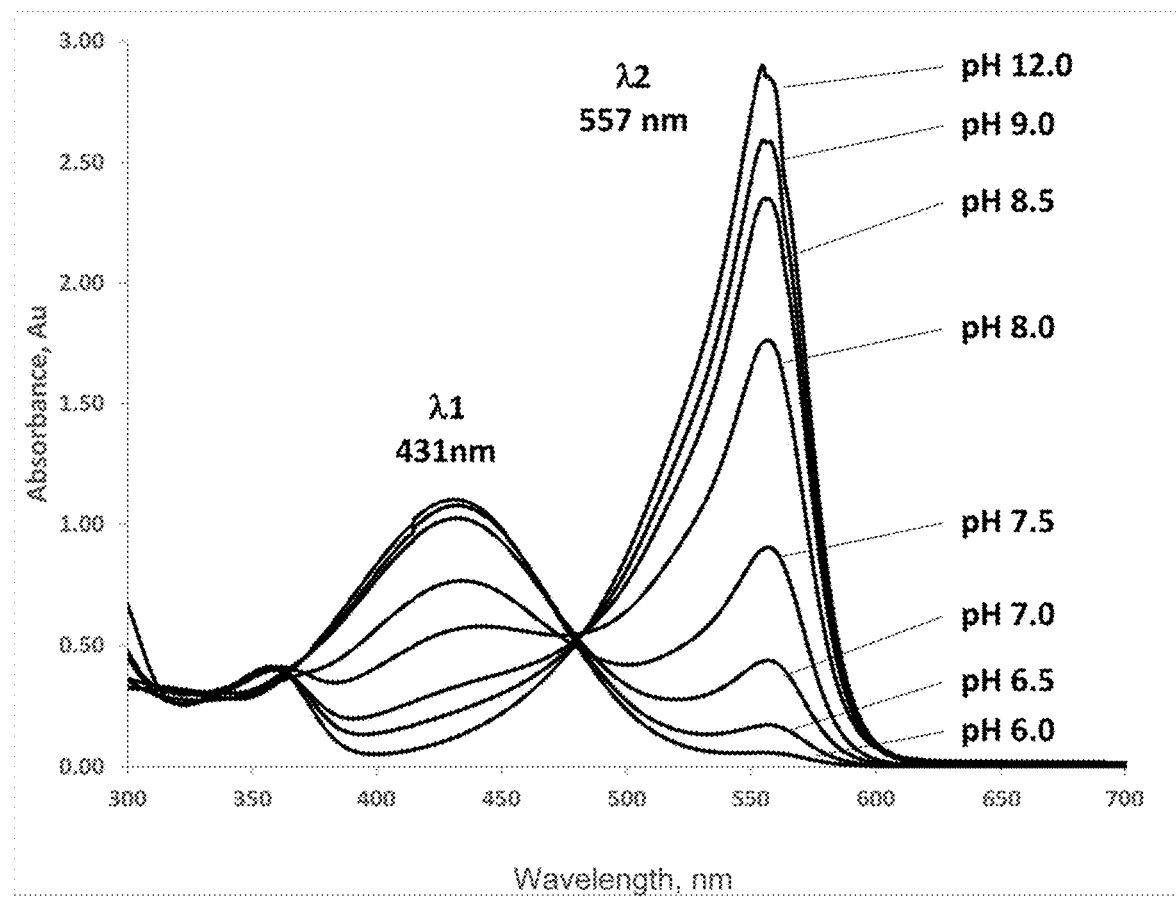
FIG. 1 presents the UV-Vis spectrum of phenol red as a function of pH.

The present invention provides modified indicator compounds which can covalently bond to a substrate. These modified indicator compounds overcome the limitations of adsorbed dyes.

In a principal embodiment, the invention provides materials and methods for covalent attachment of an indicator dye to a substrate, and the resulting derivatized substrates and their use for monitoring one or more characteristics of a water sample. Covalent bonding of the indicator to the substrate prevents desorption of the indicator compound and allows for significantly greater stability for long term storage in contact with, or in the vicinity of, water. As shown in the Examples, testing of certain embodiments of the derivatized substrates of the invention has demonstrated the superiority of this approach and the utility for an automated system which relies on an electronic spectral reader for the determination of a specific chemistry value based upon chemical changes to an appropriate dye.

Covalent conjugation of an indicator compound, such as a chemically reactive dye, to a suitable substrate offers significant advantages over adsorbed dyes. Modifying such dyes to allow for covalent bonding to a substrate, however, causes a number of changes in dye properties that need to be considered. Changing the electronic structure of any molecule will result in a change in its absorbance and reflectance spectra. This is an important consideration since either spectral reflectance or absorbance can be used in a spectrophotometric pad reader. Additionally, changing the structure of a suitable dye may alter its response characteristics. For example, the pKa of a pH sensitive dye may change upon modification and bonding to a substrate, thereby changing the useful range of that dye for pH measurement.

The present invention provides methods of producing derivatized indicator compounds and their covalent attachment to a substrate that retain useful spectral characteristics of the indicator compound.

Indicator Compounds and Modification Thereof

Indicator compounds of use in the present invention are organic pH indicator dyes which are weak acids with distinct spectral properties associated with protonated dye acid (HA) and its conjugate base (A⁻) forms. The HA and A⁻ concentrations are related by the Henderson-Hasselbalch equation:

pH=pKa+log[A⁻]/[H—A]

where Ka is the acid dissociation constant, pKa is −log Ka, and [A⁻] and [HA] are the concentrations of dissociated and undissociated dye acid form, respectively.

Suitable indicator compounds of use in the methods and compositions of the invention include those which react with formaldehyde or paraformaldehyde to form a reactive compound. Such indicator compounds include, but are not limited to, phenolic dyes, preferably phenolic dyes having at least one CH group in the phenol moiety which is adjacent (ortho) to the phenolic —OH group. Such phenolic dyes include phenol red, cresol red, m-cresol purple, xylenol blue, thymol blue and chlorophenol red. In preferred embodiments, the indicator compound is phenol red. Such phenolic dyes can be modified by reaction with formaldehyde or aldehydes to introduce functional groups suitable for chemical bonding to hydroxylated polymers, such as those discussed below, as well as polymers comprising aromatic groups.

In preferred embodiments, the indicator compound is a sulfonephthalein dye (SPD). Such compounds are commonly used as pH sensitive indicators for determination of pH of aqueous solutions. Examples of pH sensitive SPDs useful as pH indicators include, but are not limited to, phenol red, cresol red, m-cresol purple, xylenol blue, thymol blue, chlorophenol red, bromophenol blue, bromocresol purple, bromocresol green, bromothymol blue, xylenol orange, and methylthymol blue. The structure of suitable SPDs and their conjugate bases are shown generically below, and their spectral and chemical properties are reported in Table 1.

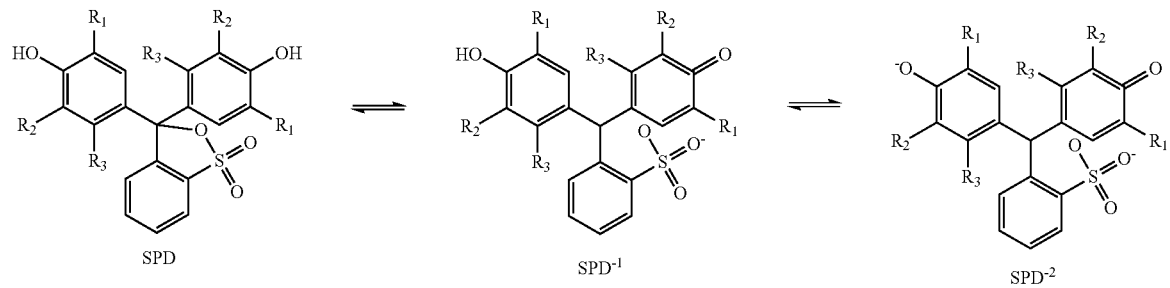

TABLE 1

SPD derivative UV-Vis spectral and chemical properties

| SPD derivative | R₁ | R₂ | R₃ | λ1, nm | λ2, nm | pKa* SPD⁻¹/SPD⁻² |
|---|---|---|---|---|---|---|
| Phenol Red (PR) | H | H | H | 431 | 557 | 7.4 |
| Cresol Red (CR) | Me | H | H | 430 | 565 | 8.3 |
| m-Cresol Purple (mCrP) | H | H | Me | 432 | 578 | 8.3 |
| Xylenol Blue | Me | H | Me | 436 | 594 | 8.5 |
| Thymol Blue | i-Pr | H | Me | 432 | 595 | 8.9 |
| Chlorophenol Red (ClPR) | Cl | H | H | 436 | 575 | 6.7 |
| Bromophenol Blue | Br | Br | H | 436 | 591 | 4.1 |
| Bromocresol Purple (BrCrP) | Br | Me | H | 432 | 589 | 6.3 |
| Bromocresol Green (BrCrG) | Br | Br | Me | 432 | 614 | 4.7 |
| Bromothymol Blue | i-Pr | Br | Me | 427 | 602 | 7.1 |
| Xylenol Orange | CH₂N(CH₂COOH)₂ | H | Me | 436 | 583 | Multiple pKa's pH 6.0-11.7 |
| Methylthymol Blue | CH₂N(CH₂COOH)₂ | iPr | Me | 442 | 614 | Multiple pKa's pH 6.0-13.0 |

Unmodified SPDs have been used for the preparation of pH sensitive indicators adsorbed on the surface of suitable polymeric materials, such as cellulose based materials. Adsorbed SPDs have good pH response and sensitivity in a pH range, typically, close to the pKa corresponding to the SPD⁻¹/SPD⁻² transition. Depending on the particular SPD selected, the pKa for the SPD⁻¹/SPD⁻² transition varies from approximately 4 to more than 9. Phenol red (PR) has a pKa of approximately 7.4. In general, substitution with electron acceptor substituents (e.g., Cl, Br in the C2/C5 positions) results in a pKa shift to a lower pH range relative to PR, and substitution with electron donor substituents (e.g., C₁-C₃ alkyl in the C2, C4 and C5 positions) results in a pKa shift to a higher pH range. Mixed substitution with electron donor and acceptor substituents provides dyes that have pKa's similar to phenol red and are therefore useful at a pH range around neutral. Examples of such SPDs include bromocresol purple and bromothymol blue.

Figure 2:
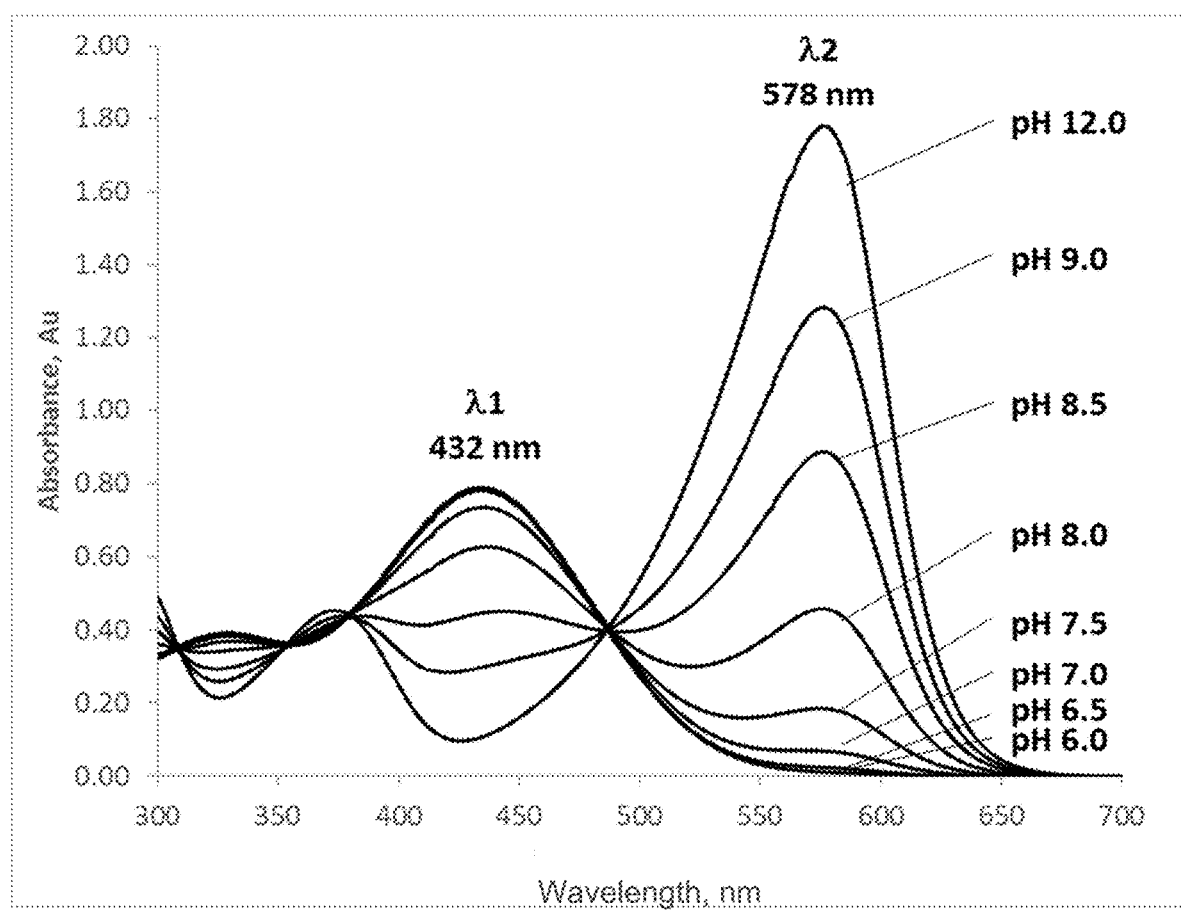
FIG. 2 presents the UV-Vis spectrum of m-cresol purple as a function of pH.

The representative UV-Vis spectral profiles of phenol red and m-cresol purple as a function of pH are shown in FIGS. 1 and 2 respectively. Measurement of absorbance at specific wavelengths allows for the determination of the concentrations of the acidic and basic forms of the dye. These wavelengths are typically selected based upon the absorbance maxima for each specific dye, although other wavelengths can be employed albeit with diminished sensitivity. The position of the pH sensitive wavelengths λ1 and λ2 corresponding to the SPD forms $SPD^{-1}$ and $SPD^{-2}$ are reported in Table 1.

The $SPD^{-1}$ associated signal λ1, shows low pH (acid condition) variability and is observed typically in 425-435 nm range. The position of SPD signal λ2 varies significantly depending on SPD substitution, ranging from approximately 557 nm (PR) to 614 nm (BrCrG) and is most sensitive to changes in the electronic structure at high (basic) pH conditions. Substitution with electron donor substituents only slightly increases the λ2 value (i.e., $R_1$ is Me in CR, and $R_2$ is Me in mCR), while introduction of electron acceptors results in significant λ2 shift to longer wavelengths (BrCrG, ClPR).

In certain embodiments, the indicator compound is derivatized by addition of a functional group that is capable of forming a covalent bond to a substrate. In preferred embodiments, the indicator compound is derivatized by reaction with an aldehyde, preferably formaldehyde.

In certain embodiments, the indicator compound is an SPD, such as phenol red, cresol red, m-cresol purple, xylenol blue, thymol blue or chlorophenol red, and is derivatized by reaction with an aldehyde, preferably formaldehyde or paraformaldehyde. This reaction can, for example, be carried out in basic aqueous solution, preferably under conditions which minimize the formation of multimeric SPD/formaldehyde adducts. The reaction is preferably quenched by addition of acid, and the derivatized dye can be used as is or isolated. The derivatized SPD can then be dissolved in a suitable solvent, and the substrate is treated with the resulting solution under conditions suitable for reaction of the hydroxymethyl groups of the derivatized SPD with functional groups on the substrate, such as hydroxyl groups and phenyl groups. This process is illustrated in the scheme below, wherein the SPD is phenol red.

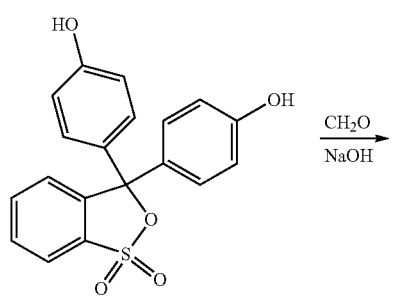

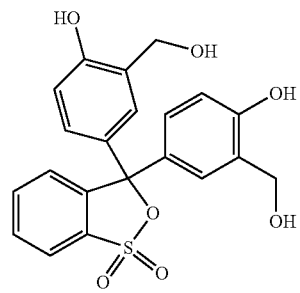

Modified SPD compounds of the invention include compounds of Formula (I)

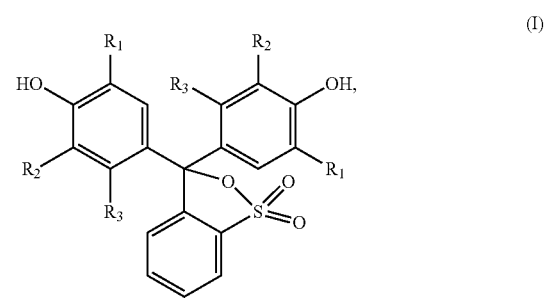

wherein $R_1$, $R_2$ and $R_3$ for each compound are set forth in Table 2.

TABLE 2

| Parent SPD | $R_1$ | $R_2$ | $R_3$ |
| --- | --- | --- | --- |
| Phenol Red (PR) | $HOCH_2$— | H | H |
| Cresol Red (CR) | Me | $HOCH_2$— | H |
| m-Cresol Purple (mCrP) | $HOCH_2$— | H | Me |
| m-Cresol Purple (mCrP) | H | $HOCH_2$— | Me |
| Xylenol Blue | Me | $HOCH_2$— | Me |
| Thymol Blue | i-Pr | $HOCH_2$— | Me |
| Chlorophenol Red (ClPR) | Cl | $HOCH_2$— | H |
| Xylenol Orange | $CH_2N(CH_2COOH)_2$ | $HOCH_2$— | Me |

In other embodiments, the indicator compound, for example an SPD, preferably phenol red, is modified by substitution with a carboxyl or primary amino group where such group is preferably attached to the indicator compound via a linker, such as a straight chain or branched $C_1$-$C_6$ alkylene, preferably a straight chain or branched $C_2$-$C_6$ alkylene, and more preferably a straight chain $C_2$-$C_6$ alkylene. Suitable modified SPD compounds include those represented by Formula II,

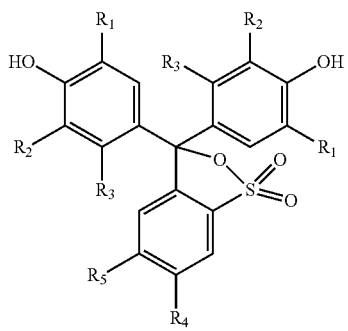

(II)

where the combinations of $R_1$, $R_2$ and $R_3$ are as set forth in Table 1, one of $R_4$ and $R_5$ is hydrogen and the other is $NH_2$-Linker or HOOC-linker—wherein the linker is as defined above. Preferably, one of $R_4$ and $R_5$ is hydrogen and the other is amino-$C_1$-$C_6$-alkyl, preferably 2-aminoethyl (—$CH_2CH_2$—$NH_2$), or carboxy-$C_1$-$C_6$-alkyl, preferably 3-carboxy-n-propyl (—$(CH_2)_3$—COOH). In particularly preferred embodiments, the modified SPD is represented by one of formulas (IIa) and (IIb) below.

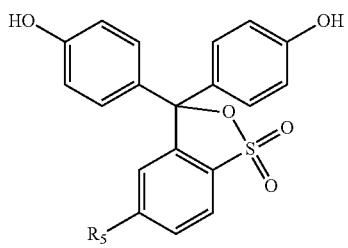

(IIa)

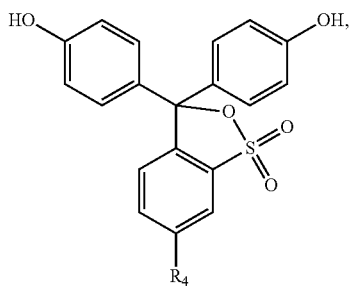

(IIb)

where $R_4$ and $R_5$ are as defined above, provided that $R_4$ in Formula (IIb) and $R_5$ in Formula (IIa) are not hydrogen. The modified SPD can either be a substantially pure compound of Formula (II) or a mixture of two or more compounds of Formula (II). In one embodiment, the modified SPD is a mixture of one or more compounds of Formula (IIa) and one or more compounds of Formula (IIb).

In another embodiment, the indicator compound is a fluorescent pH indicator. A variety of fluorescent organic dyes with pH-dependent optical properties are known in the art and can be used for pH monitoring by means of fluorescence spectroscopy techniques relying on dye fluorescence analysis such as steady-state fluorescence spectroscopy and fluorescence lifetime measurements. Examples of commonly used fluorescent pH indicators are: 6- and 5-carboxyfluorescein and 6- and 5-aminofluorescein derivatives; 2',7'-bis-(2-carboxyethyl)-5-(and-6)-carboxyfluorescein; 1,4-dihydroxyphthalonitrile, 8-hydroxypyrene-1,3,6-trisulfonic acid (HPTS); 7-(diethylamino)-1,2-benzophenoxazine derivatives (i.e., ETH 5350 and Nile Blue); carboxynaphthofluorescein derivatives seminaphthorhodafluorescein (SNARF) and seminaphthofluorescein (SNAFL); boron-dipyrromethene (KBH-01) dye derivatives; aminocyanine dye derivatives. The pH sensitive range for these fluorescent indicators vary broadly in pH 2-12 range based on pKa of the dye derivative and can be easily tuned to the range of interest based on specific modification of the dye scaffold.

An example of modification of 8-hydroxypyrene-1,3,6-trisulfonic acid as its sodium salt is shown below. The 8-hydroxypyrene-1,3,6-trisulfonic acid can also be modified as a salt of a cation other than sodium, such as potassium or ammonium. This compound is suitable as a pH sensitive probe for pH range of 7.0-8.0 for red, green and blue combination photodiode (RGB) detectors with maximum sensitivity at 460 nm/520 nm/630 nm.

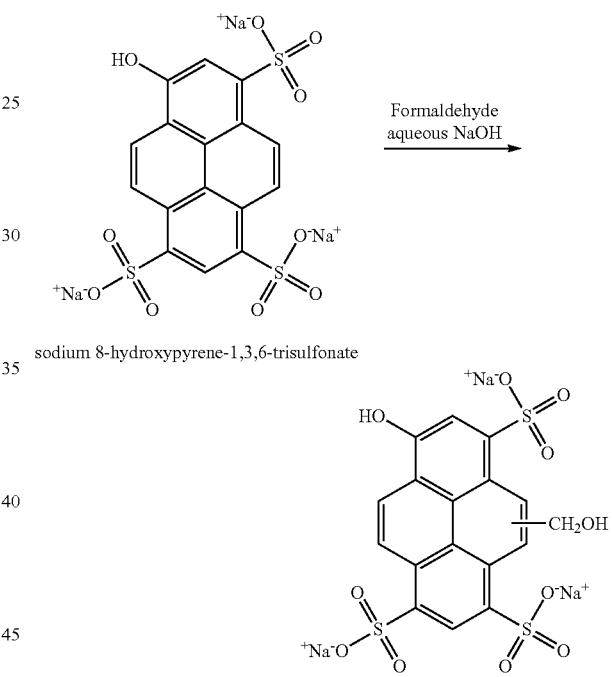

Figure 7:
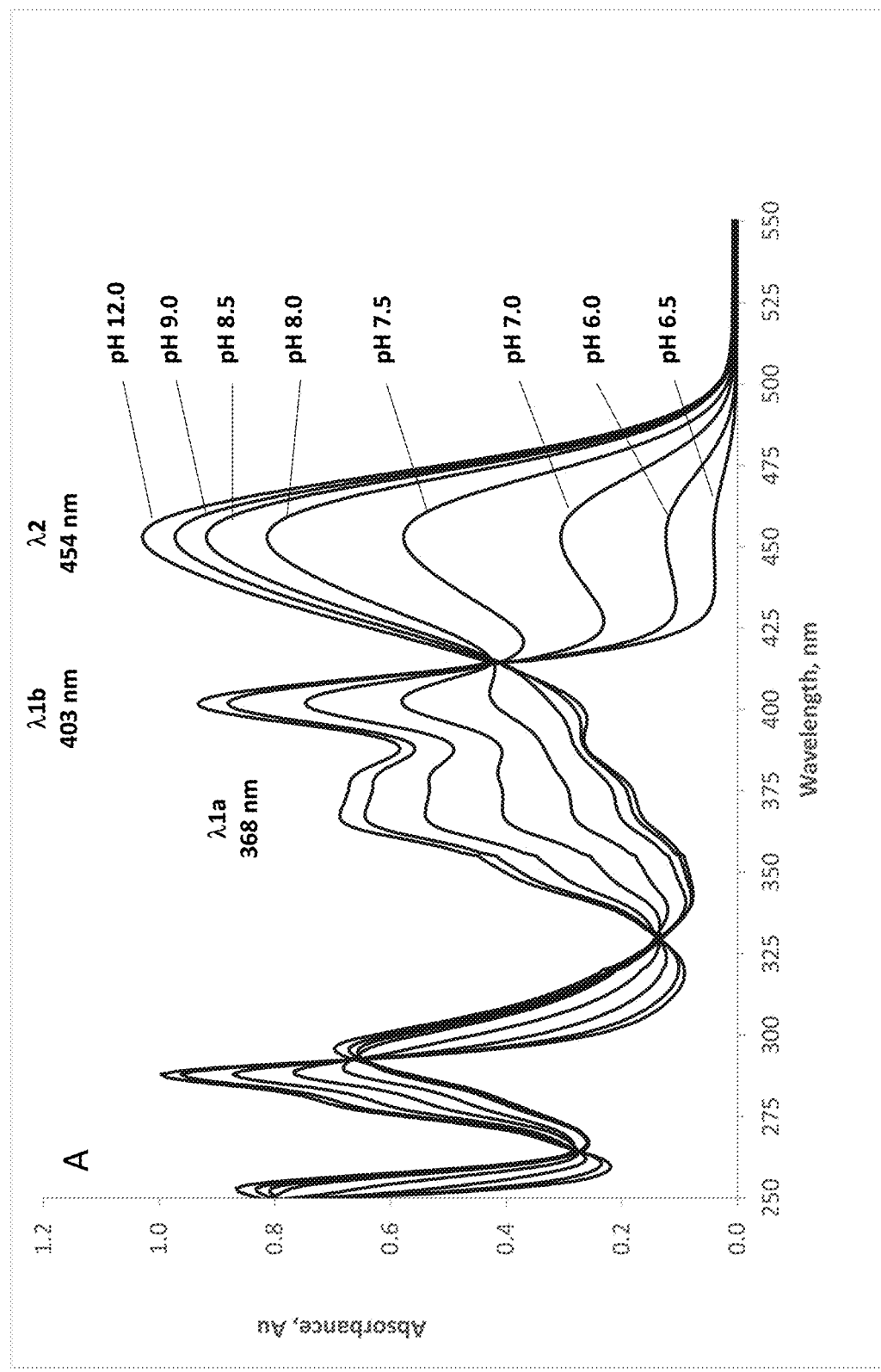
FIG. 7 presents the UV-Vis spectra of HPTS as a function of pH.
Figure 8:
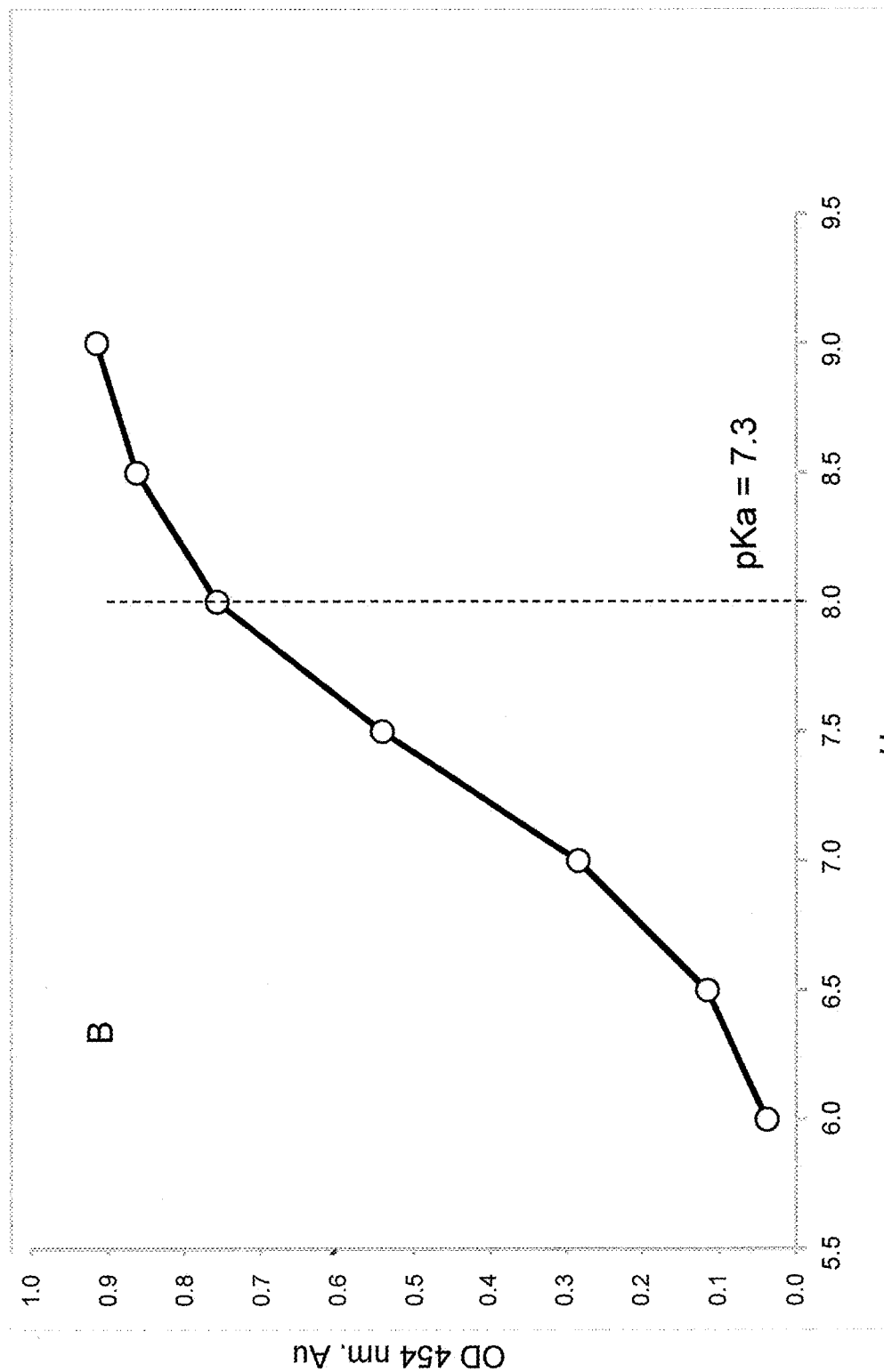
FIG. 8 illustrates the HPTS pH response range at 454 nm.

The UV-Vis spectrum of HPTS as a function of pH is shown in FIG. 7, while the pH response range for this dye at 454 nm is shown in FIG. 8.

Another example of a fluorescent pH sensitive indicator compound include probe based on pH mediated intra-molecular association and inter-molecular aggregation of amphiphilic polymer immobilized fluorescent dyes. A conformational transition of amphiphilic polymer system in response to pH change in these systems results in collapse of water-soluble polymer into a compact globular or hypercoil structure bringing the fluorophore molecules into close proximity with one another. This results in a dramatic reduction in fluorescence intensity and fluorescent lifetime of the fluorophore dyes immobilized on the polymer scaffold allowing an accurate pH measurement. Examples of these systems include amphiphilic poly(l-lysine iso-phthalamide) polymers incorporating low levels of bis-functional of Cy3 and/or Cy5 dyes via the l-lysine moiety.

Substrates

The substrate can be a pure material, or a mixture of materials, such as a composite. In one embodiment, the substrate comprises a first core material which is coated with a second material. The substrate is preferably formed of a polymer, such as a crosslinked polymer. The substrate preferably has functional groups which can react with the derivatized indicator compound to covalently conjugate the indicator compound to the substrate. The functional groups of the substrate are preferably located on the surface of the substrate and/or in a region or regions of the substrate that are accessible to a solution comprising the derivatized indicator compound, such as within the pores of a porous substrate or within the volume of a hydrophilic polymeric coating. The indicator compound can be bonded to any and all layers of a multilayered substrate or throughout the depth of the material in the case of a hydrogel or hydrophilic polymer.

In certain embodiments, the substrate comprises a hydroxylated polymer. A variety of hydroxyl containing polymers are known in the art, including cellulose, cellulose derivatives, polyvinyl alcohol, derivatives of polyvinyl alcohol, polyallyl alcohol and derivatives of polyallyl alcohol. Additionally, aldehyde modified dyes can be reacted with a wide range of other polymers, for example those containing aromatic groups such as polyethylene terephthalate (PET), polystyrene or other aromatic polymers well known to those skilled in the art. Many polymers contain aromatic rings and are therefore suitable for immobilization of the modified indicator dyes.

A substrate core having a hydrophobic or non-functionalized surface, such as PET, is preferably coated with a second, hydrophilic material. Such a hydrophilic coating can serve to adsorb water, making the sensing pad more responsive to the water chemistry and provide for greater attachment of the dye to the substrate to increase the response. For example a substrate core can be coated with poly(vinyl alcohol), which can adsorb water and also provides hydroxyl groups for covalent conjugation of the derivatized dye. Alternatively, if more dye is desired to be bonded to the surface, a woven, porous or rough substrate can be used to provide greater surface area for dye bonding.

In other cases where the dye concentration need not be maximized, the indicator can be bonded to only the surface of a nonporous polymer or woven/nonwoven variant. Surface immobilization provides a very efficient means of dye utilization.

In cases where the reflectance spectrum will be used to determine the chemical state of the dye, a white opaque substrate is preferred since its reflectivity is the highest and there is no background color to interfere with the spectral reading. Even with a white substrate, however, spectral correction may still be required as the reflectivity of the substrate may vary due to small differences in scattering and color. Colored substrates can also be employed but correction for the background color would be required to accurately allow for the determination of the state of the dye with regards to its analyte concentration. A reflective substrate can be used to increase the amount of light used for detection of the state of the dye. For example, aluminized PET or nylon can be used where the aluminum coating is on the back side of the substrate, therefore allowing the dye to bond to the organic substrate while providing incident light to be reflected back to the detector while passing through the dye layer.

Alternatively, a clear or transparent substrate can be used to allow for the determination of an absorption spectrum as opposed to a reflectance spectrum. A transparent substrate may be composed of a single substance or multiple substances. The materials may be either organic or inorganic. An organic coating may also be applied to an inorganic substrate. For example, a poly(vinyl alcohol) coating may be applied to a glass substrate. Both substances are clear allowing for the absorption spectrum to be determined.

Without being bound by theory, it is believed that the derivatized indicator compound, such as derivatized phenol red, reacts with available substrate hydroxyl groups as shown in the scheme below to form an ether group which covalently attaches the derivatized phenol red molecule to the substrate.

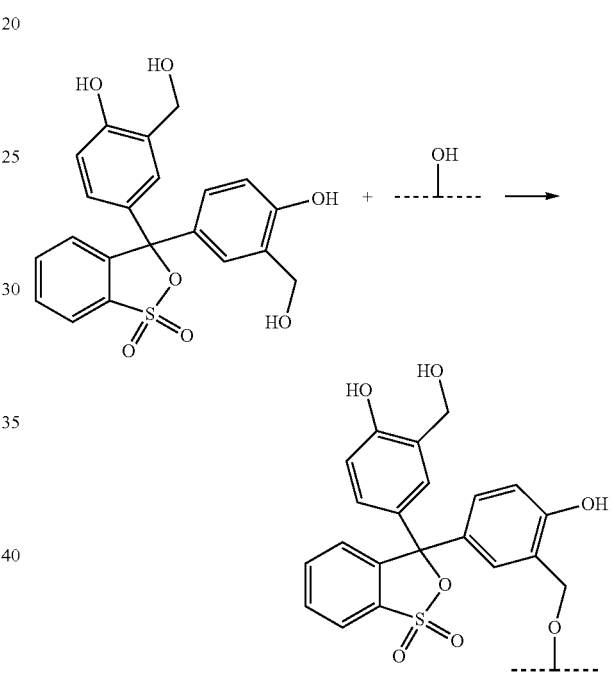

The derivatized indicator compound can also be covalently attached to a suitable substrate by formation of an ester or amide linkage. For example, an indicator compound, such as an SPD, can be derivatized with carboxyl or amino groups as described above. These groups can react with hydroxyl groups, carboxyl groups or amino groups on the substrate surface to form amide or ester groups which covalently link the indicator compound to the substrate.

In another embodiment, the derivatized indicator compound can react with itself to form oligomers or polymers. The indicator compound can, for example, be polymerized in the presence of the substrate to form a coating on the substrate. This coating can be covalently attached to the substrate, for example, via one monomeric unit, or can simply form a layer on the substrate surface without covalent bonding. The formation of oligomers and polymers can occur as shown in the scheme below for phenol red, in which the hydroxymethylated dye molecule reacts with an underivatized dye molecule to first form a dimer, which can further react with derivatized monomers or other dimers to form oligomers.

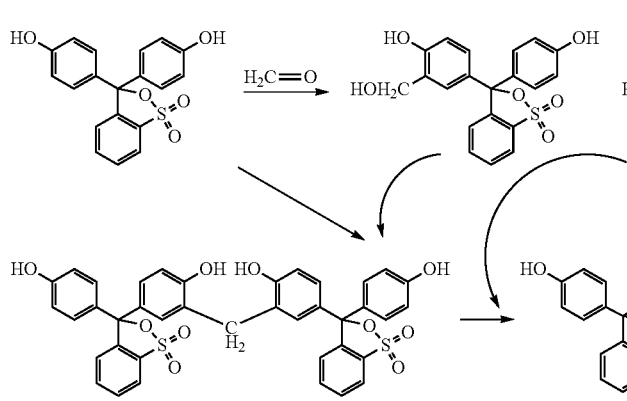
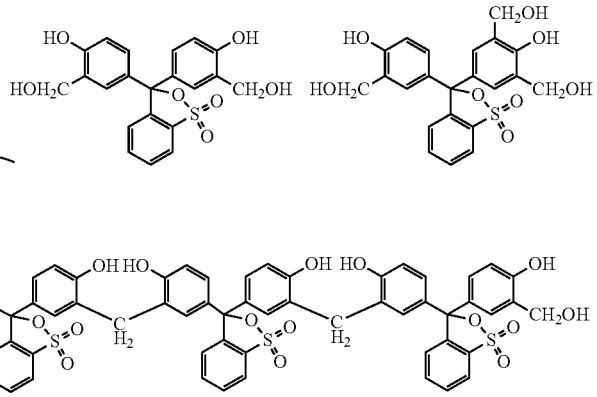

Uses of Indicator Compound Derivatized Substrates

The indicator compound derivatized substrates can be used to monitor the chemical parameters, such as pH, of recreational waters. In particular, the substrates, or pads comprising these substrates, can remain in contact with water for extended periods of time without losing their effectiveness. In preferred embodiments, the derivatized substrate of the invention is a component of a device that determines the protonation state of the modified indicator by UV/Vis absorbance, transmission or reflection, or by fluorescence.

Testing of water samples can be done, for example, in an automated reader or using a reflectance spectrophotometer. In one embodiment, the automated reader comprises an RGB detector. In certain embodiments, the RGB detector has three light emitting diodes with peak energies at 460 nM (blue, B), 515 nM (green, G) and 630 nM (red, R). In other embodiments, the RGB detector has three light emitting diodes with peak energies at 460 nM (blue, B), 520 nM (green, G) and 630 nM (red, R). The ratio (G-R)/(B-R) can be used to determine the pH, or, preferably, the absorbance values at the different wavelengths are used according to the equation $$\log_{10}[(G/R)*(R_w/G_w)*(G_s/R_s)]/\log_{10}[(B/R)*(R_w/B_w)*(B_s/R_s)].$$

In other embodiments, a simple ratio is used to translate reflected light intensities to the corresponding pH of the contacting solution. The ratio of (R-G)/(R-B) is used to allow for the correction of the background where R is employed as the control wavelength and is calibrated using an identical substrate which does not have dye immobilized onto it. This is important if there are no internal or external standard that is employed. The R correction allows for variation in the distance between the pH pad and the reader as well as other artifacts that may be apparent in an automated device.

The selection of a modified indicator compound, such as a modified SPD, for use in a particular situation and with a particular detection system will depend on its spectral properties and the pH dependence of these properties. For example, the parameters $\lambda 2$ and OD 430 $nm^{pH6.0}$/OD 430 $nm^{pH9.0}$ are parameters for the selection of an SPD candidate for an RGB-based optical pH photosensor design. The shift in the position of $\lambda 2$ away from the maximum sensitivity of the photodiode "Green" channel reduces the RGB photodiode sensitivity to pH changes, independently, the reduction in 430 $nm^{pH6.0}$/OD 430 $nm^{pH9.0}$ parameter value results is reduction of overall SPD dye coating sensitivity to pH change in pH range 6.0-9.0, which corresponds to the working range of the SPD-based photosensor.

A suitable automated reader in which the derivatized substrates of the invention can be employed is marketed by WaterGuru, Inc.

Unless otherwise defined, all technical and scientific terms used herein are accorded the meaning commonly known to one with ordinary skill in the art. All publications, patents, published patent applications, and other references mentioned herein are hereby incorporated by reference in their entirety.

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, Formulations and/or methods of the invention may be made without departing from the spirit of the invention and the scope of the appended claims.

EXAMPLES

Example 1

Synthesis of Modified Phenol Red

Reagents
Formaldehyde solution 37% (Sigma-Aldrich cat #8187081000)
Phenol red, MW 354.38 (Sigma-Aldrich cat #114529)
37% Hydrochloric acid, ACS reagent (Sigma-Aldrich cat #320331)

A representative procedure for the synthesis of SPD formaldehyde adducts is given below for phenol red dye. In a 50-mL flask equipped with condenser, magnetic stirring bar and nitrogen inlet was charged with phenol red, FW 354.38, (0.71 g, 2.0 mmol), sodium hydroxide (0.5 g, 12.5 mmol) and distilled water (6.0 mL). After 5 minutes of agitation 4.0 mL of 37% aqueous formaldehyde solution (approximately 24.7 mmol), were added. The reaction flask was placed in an oil bath preheated to 110° C. and the condensation reaction was carried at under reflux conditions in nitrogen atmosphere. After 2 hours of reflux, the resulting solution was cooled down to ambient temperature and 37% hydrochloric acid (2.0 mL) was added dropwise to precipitate phenol red formaldehyde adduct. The precipitate was collected on glass fiber filter and dried in vacuum at ambient temperature for 48 hours. After drying 0.52 g of formaldehyde modified phenol red (PRm) was collected. Obtained PRm material was stored at −20° C.

Figure 3:
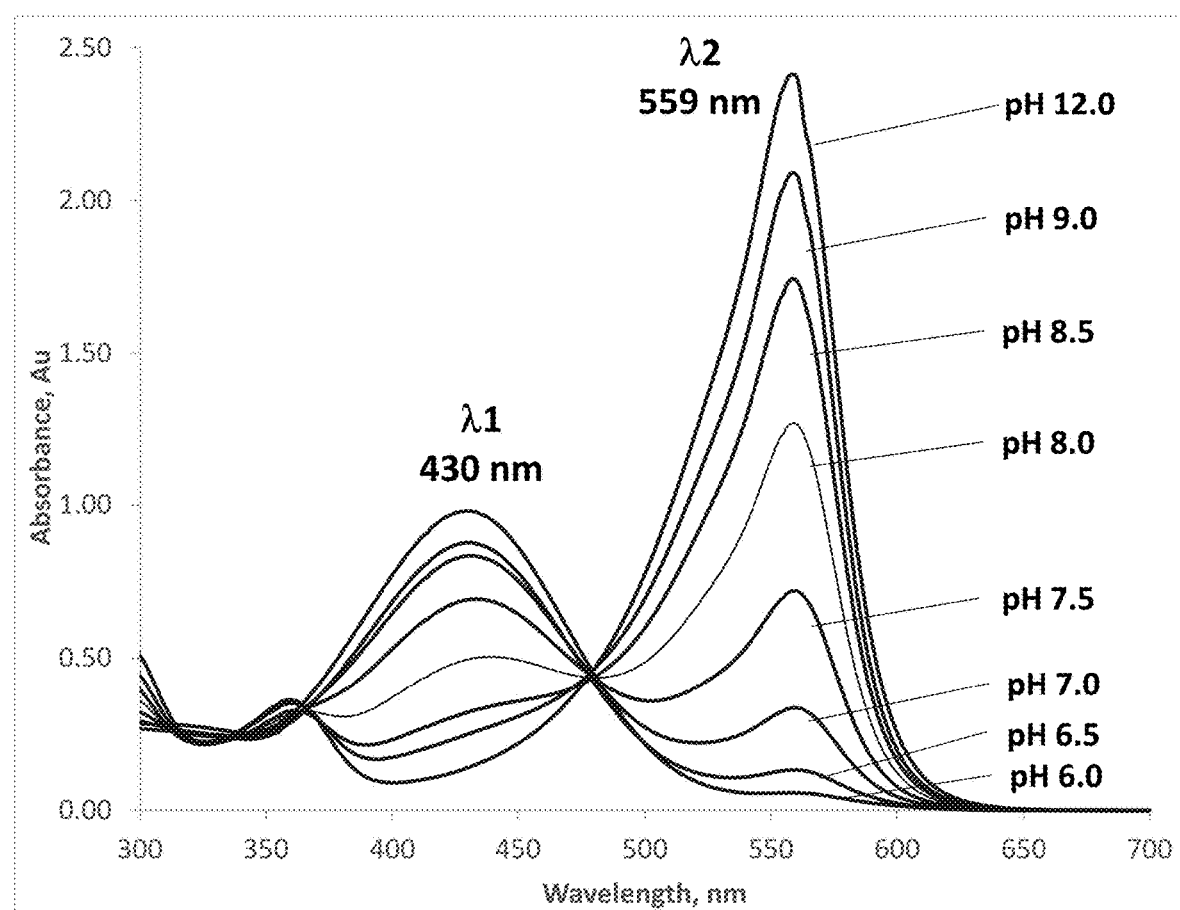
FIG. 3 presents the UV-Vis spectrum as a function of pH of phenol red modified with formaldehyde as described in Example 1.
Figure 4:
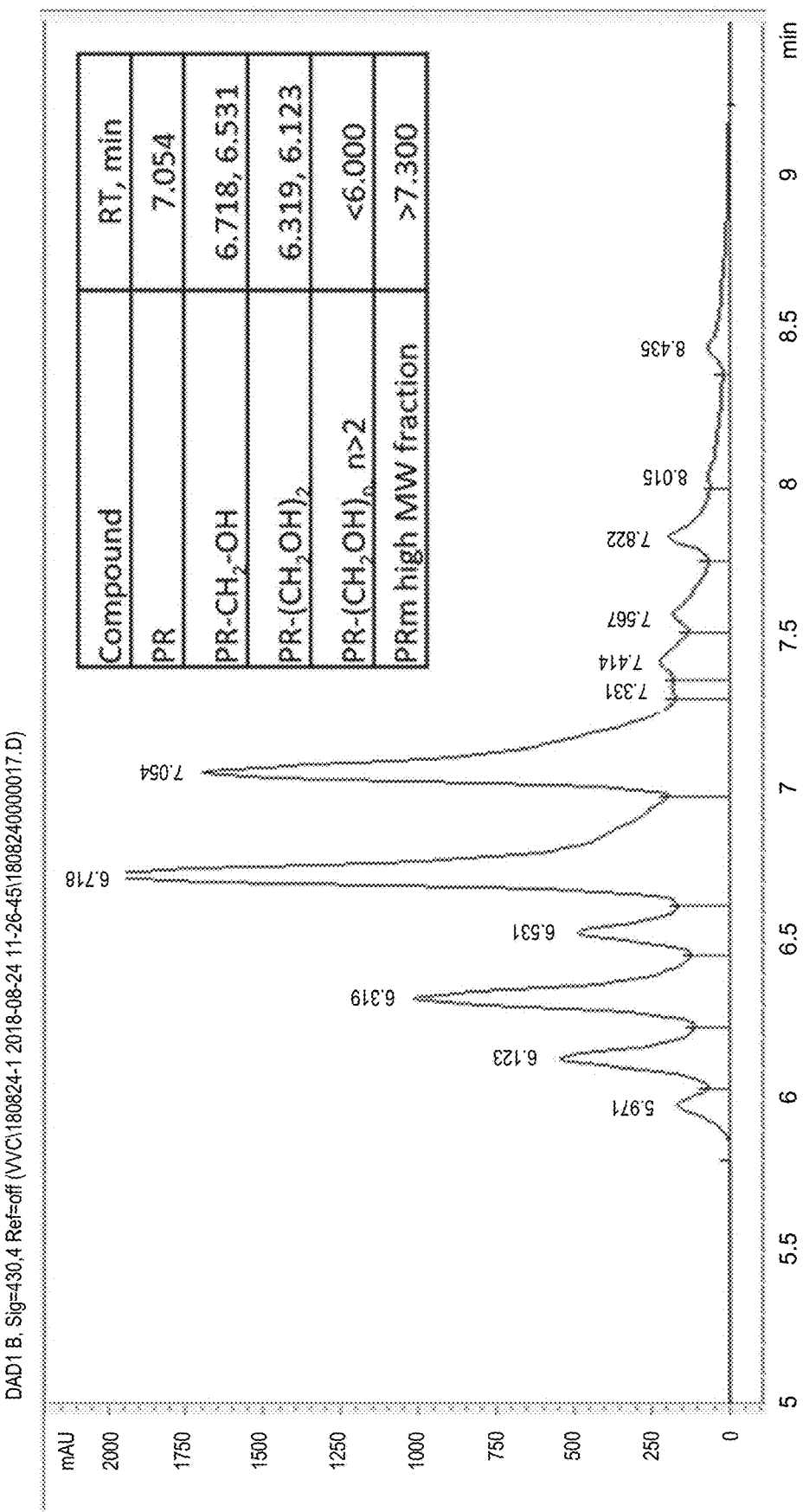
FIG. 4 presents the RP HPLC profile of phenol red modified with formaldehyde as described in Example 1.

SPDm formaldehyde adducts obtained as the result of the condensation reaction of the corresponding SPD dye with formaldehyde, typically, contain a mixture of the positionally substituted SPD methylol derivatives as well as small quantities of their higher molecular weight condensation products and unmodified SPD. The PRm dye UV-vis spectra as a function of pH was determined in 0.1 M sodium phosphate buffers in a pH range of 6.0 to 12.0, and the results are shown in FIG. 3. The analysis of composition of the representative phenol red mixed formaldehyde adduct (PRm) performed by RP HPLC with UV-Vis detection at 430 nm is shown in FIG. 4.

For mono- and di-substituted SPD dyes the substitution of the core SPD structure with single or multiple methylol groups resulted in a) an increase of pKa for the corresponding $SPD^{-1}/SPD^{-}$ transition and 2) a shift of $\lambda 2$ of SPDm derivatives to the longer wavelength. The effect of derivatization of phenol red on pKa and spectral properties is shown in Table 3.

TABLE 3

Phenol Red derivative UV-Vis properties

| PR derivative | λ1, nm | λ2, nm | pKa | $\lambda 1^{pH\ 6/pH\ 9}$ Abs ratio |
|---|---|---|---|---|
| Phenol Red (PR) | 431 | 557 | 7.4 | 5.1 |
| Monomethylol phenol red (PR1) | 430 | 565 | 7.4 | 5.5 |
| Dimethylol phenol red (PR2) | 429 | 565 | 8.6 | 1.8 |
| Phenol red mixed formaldehyde adduct (PRm) | 430 | 559 | 7.8 | 3.9 |

*) "$\lambda 1^{pH\ 6/pH\ 9}$ Abs ratio" is calculated as OD 430 $nm^{pH\ 6.0}$/OD 430 $nm^{pH\ 9.0}$ For the monomethylol PR derivative (PR1) the extinction coefficient of λ1, at the maximum $SPD^{-1}$ concentration, and λ2, at the maximum PR derivative $SPD^{-2}$ concentration, do not change significantly compared to unmodified PR and remained approximately in 10,000 $mol^{-1}L^{-1}$ cm and 20,000 $mol^{-1}L^{-1}$ cm for λ1 and λ2, respectively. To the contrary, the dimethylol PR derivative (PR2) exhibited a significant change in $SPD^{-1}/SPD^{-2}$ transition equilibrium and results in an increase in pKa and reduced λ1 and λ2 pH dependent responses in the range of interest (pH 6.0-9.0).

Considering the very low variability of λ1 position, the parameter "$\lambda 1^{pH6/pH9}$ absorbance ratio" calculated as OD 430 $nm^{pH6.0}$/OD 430 $nm^{pH9.0}$ ($\lambda 1^{pH6/pH9}$ Abs ratio) was selected as the parameter suitable for different SPD derivatives to optimize the dye response in pH range of interest (pH 6.0-9.0).

Several SPDs materials with pKa close to pH 5-8 range were selected for modification with formaldehyde to produce polyhydroxylated oligomeric reactive SPD-formaldehyde adducts (Table 4). Using the general method described above for phenol red, SPD formaldehyde mixed adducts (SPDm) were prepared by condensation of the SPD with aqueous formaldehyde in basic conditions, then the resulting mixed dye formaldehyde adducts were isolated from the reaction mixture by acidification with hydrochloric acid.

TABLE 4

SPD derivatives modified with formaldehyde.

| SPD derivative | SPD formaldehyde adduct formation |
|---|---|
| Phenol Red (PR) | Yes |
| Cresol Red (CR) | Yes |
| mCresol Purple (CrP) | Yes |
| Chlorophenol Red (ClPR) | Yes |
| Bromocresol Purple (BrCrP) | Yes |
| Bromocresol Green (BrCrG) | No |
| Bromothymol Blue (BrTB) | No |

Modification of the SPDs PR, CR, CrP, C1PR and BrCrP with formaldehyde was successful and typically resulted in substitution of the core dye structure with single or multiple methylol groups. Tri-substituted SPD derivatives BrCrG and BrTB were not active in formaldehyde condensation reaction.

Example 2

SPDm Adducts Bonding to Paper

A representative procedure for SPDm dye adducts immobilization on cellulose paper is given for phenol red mixed formaldehyde adduct (PRm). The PRm dye adduct obtained as described in Example 1 was applied to WHATMAN® Filter Paper Grade 4, disc diameter 125 mm (WFP, catalog #Z240567) at dye concentration of 0.3, 06, 075, 1.0, 1.25 and 2.5 mg/mL using treatment protocol consisting of the following steps:
 1. Immersion of WFP in PR/F aqueous solution;
 2. Removal of the excess of coating solution from filter paper by rolling glass bar applicator;
 3. Drying material in horizontal position in convection heating oven at 65° C. for 10 minutes following by incubation at 140° C. for 30 minutes;
 4. Incubation of WFP-PRm materials in 0.01N sodium hydroxide for 30 minutes following by 2×15 minutes in DI water; the pH of distilled deionized water used for paper treatment was typically in the range from pH 6.0 to pH 6.5;
 5. Material drying in convection oven at 65° C. for 10 minutes; and
 6. Resulting WFP-PRm materials were stored protected from light at ambient conditions in double sealed polyethylene bags containing silica gel desiccant.

The reflectance spectra of the resulting dry WFP-PRm materials exhibited strong PRm dye associated adsorption signal at 430 nm and week dye absorption signal about 560 nm. WFP-PRm surface reflectance ratio 560 nm/430 nm indicated that paper immobilized dye is present in the dye equilibrium state corresponding to pH of approximately 6.0-6.5.

Figure 5:
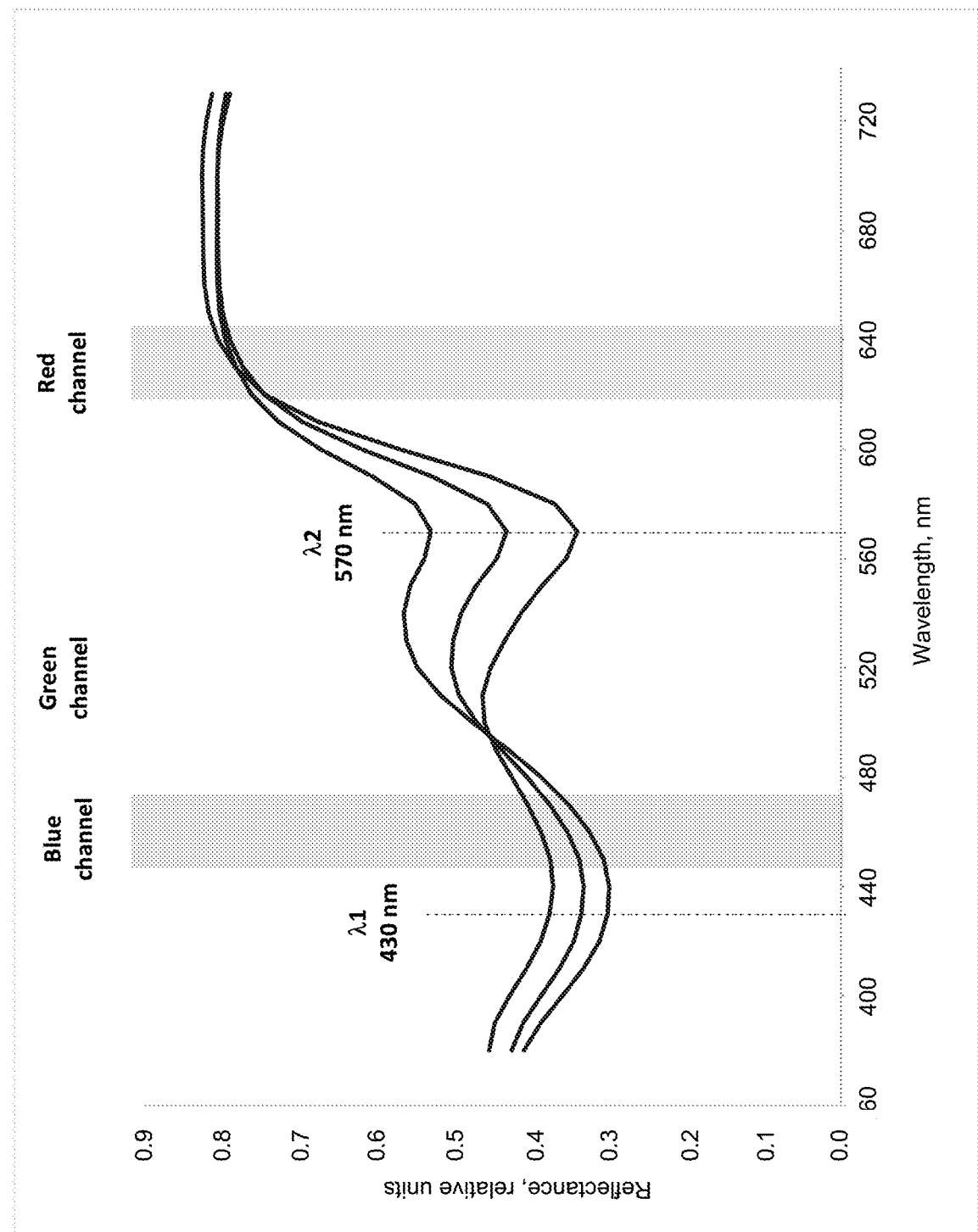
FIG. 5 presents the reflectance spectrum as a function of pH of a filter paper substrate treated with modified phenol red as described in Example 2.

A representative pH dependent reflectance profile of PRm treated Whatman paper is shown in FIG. 5. The spectra were obtained for paper treated with PRm at 0.3 mg/mL in 0.025M phosphate buffers at pH 7.0, 7.5 and 8.0. The pH response (in pH range 7.0-8.0) of Whatman Filter paper coated at different PRm dye concentration is reported in Table 5.

TABLE 5

PRm dye coated Whatman filter paper reflectance spectra pH dependence.
Reflectance response simulating RGB detector detection (630 nm/520 nm/460 nm)
calculated as $(R^{630\,nm}-G^{520\,nm})/(R^{630\,nm}-B^{460\,nm})$.

| Sample ID | Dye solution concentration, mg/mL | Reflectance Parameter | pH 7.0 | pH 7.5 | pH 8.0 |
|---|---|---|---|---|---|
| Sample 1 | 0.30 | Mean | 0.384 | 0.513 | 0.723 |
|  |  | RSD, % | 1.7% | 1.4% | 1.0% |
|  |  | % change | pH 7.5-7.0: 34% | pH 8.0-7.5: 41% | pH 8.0-7.0: 88% |
| Sample 2 | 0.60 | Mean | 0.466 | 0.617 | 0.807 |
|  |  | RSD, % | 4.0% | 6.4% | 4.3% |
|  |  | %change | pH 7.5-7.0: 32% | pH 8.0-7.5: 31% | pH 8.0-7.0: 73% |
| Sample 3 | 0.75 | Mean | 0.493 | 0.636 | 0.836 |
|  |  | RSD, % | 2.6% | 2.4% | 1.2% |
|  |  | % change | pH 7.5-7.0: 29% | pH 8.0-7.5: 32% | pH 8.0-7.0: 70% |
| Sample 4 | 1.00 | Mean | 0.512 | 0.634 | 0.841 |
|  |  | RSD, % | 2.4% | 1.2% | 0.8% |
|  |  | % change | pH 7.5-7.0: 24% | pH 8.0-7.5: 33% | pH 8.0-7.0: 64% |
| Sample 5 | 1.25 | Mean | 0.516 | 0.630 | 0.821 |
|  |  | RSD, % | 0.2% | 1.1% | 0.1% |
|  |  | % change | pH 7.5-7.0: 22% | pH 8.0-7.5: 30% | pH 8.0-7.0: 59% |
| Sample 6 | 2.50 | Mean | 0.622 | 0.732 | 0.880 |
|  |  | RSD, % | 0.2% | 0.2% | 0.1% |
|  |  | % change | pH 7.5-7.0: 18% | pH 8.0-7.5: 20% | pH 8.0-7.0: 41% |

The formaldehyde derivatives of CrR, mCrP, ClPR and BrCrP obtained in Example 1 were also applied to cellulose paper as described here for phenol red and tested for pH dependence by reflectance spectroscopy in the spectral range from 380 nm to 730 nm.

Example 3

Evaluation of PRm Dye Paper Bonding Conditions

Figure 6:
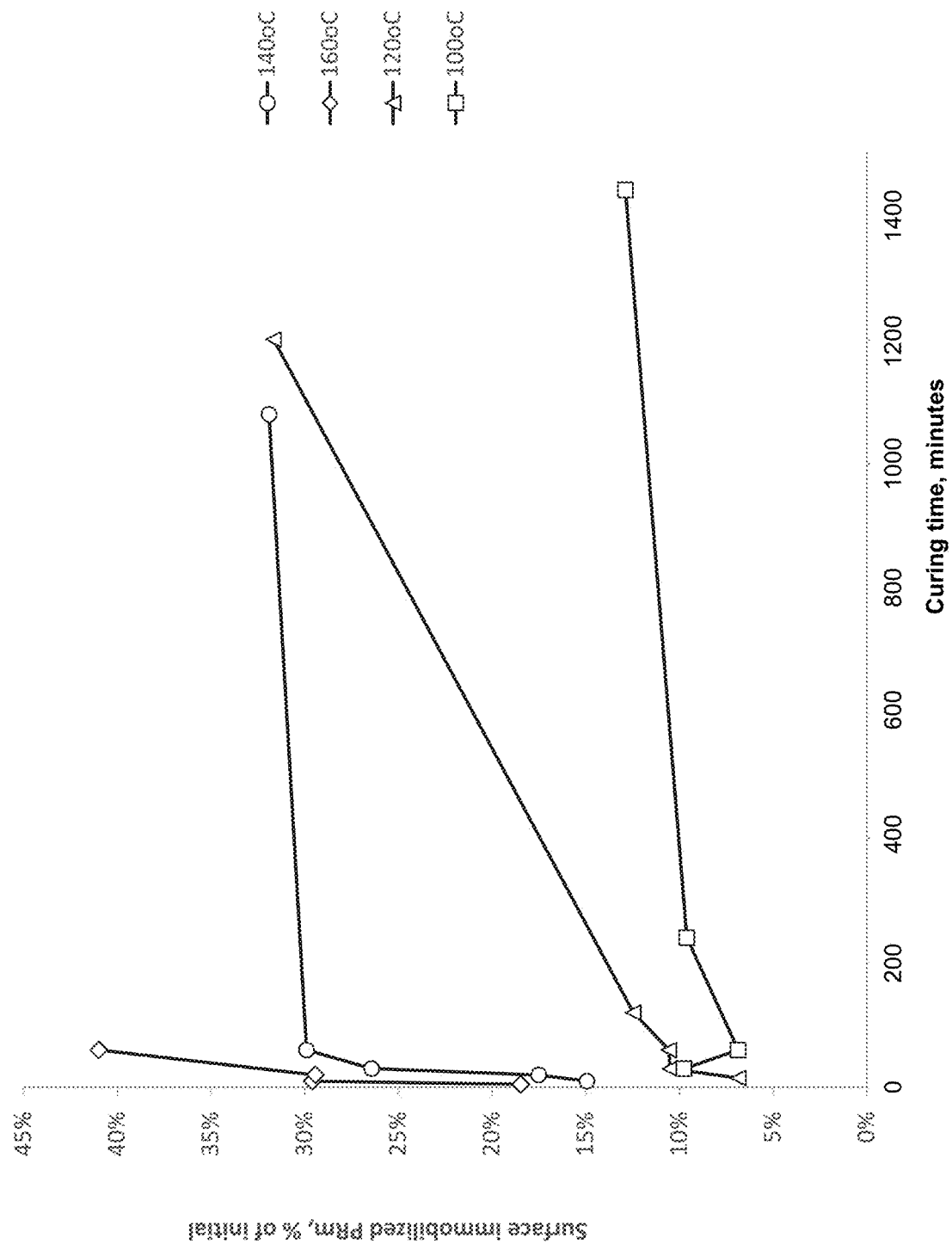
FIG. 6 is a graph of surface immobilized PRm (% of initial) on PRm-conjugated cellulose paper as a function of bonding time and reaction temperature.

Cellulose paper coupons, size 6"×8" were treated with aqueous PRm dye solution at 0.5 mg/mL. After evaporation of water (65° C., 10 minutes) dye coated samples were cut into 1"×2" coupons. Obtained PRm treated coupons were cured at 100° C., 120° C. 140° C. and 160° C. for up to 24 hours and then washed in 0.01N NaOH and DI water as described in Example 2. Alkaline washes from cured and not cured samples were analyzed spectroscopically at 430 nm for extractable dye. The percentage of paper surface bound dye was calculated for each curing condition. All treatment conditions, except 160° C./60 min, resulted dye paper coatings with suitable pH sensing properties. The best optical response in pH 7.0-8.0 range was found for PRm paper samples with approximately 30% dye bonding. Obtained dye paper bonding results are presented in FIG. 6.

Example 4

Testing of Test Papers with Covalently Attached pH Indicator Dyes

Covalent pH testing pads were evaluated using standard test conditions to simulate pool water. The chemistry of the test tank water is measured using a LaMotte spin touch system. Commercial test kits for pool water and an Oakton pH meter were used to verify the LaMotte system results. Water temperature was measured using an INK BIRD digital thermometer. After each set of measurement, the tank was refilled using fresh tap water.

Typical Test Conditions Employed Were:
Free Cl 0.01 ppm
Total Cl 0.03 ppm
Combined 0.02 ppm
pH N/A
Alkalinity 108 ppm
Hardness 228 ppm
Stabilizer 54 ppm
Copper 0.1 ppm
Iron 0 ppm
Phosphate 12 ppb
Salt 1262 ppm
Temperature 80° F.

Figure 9:
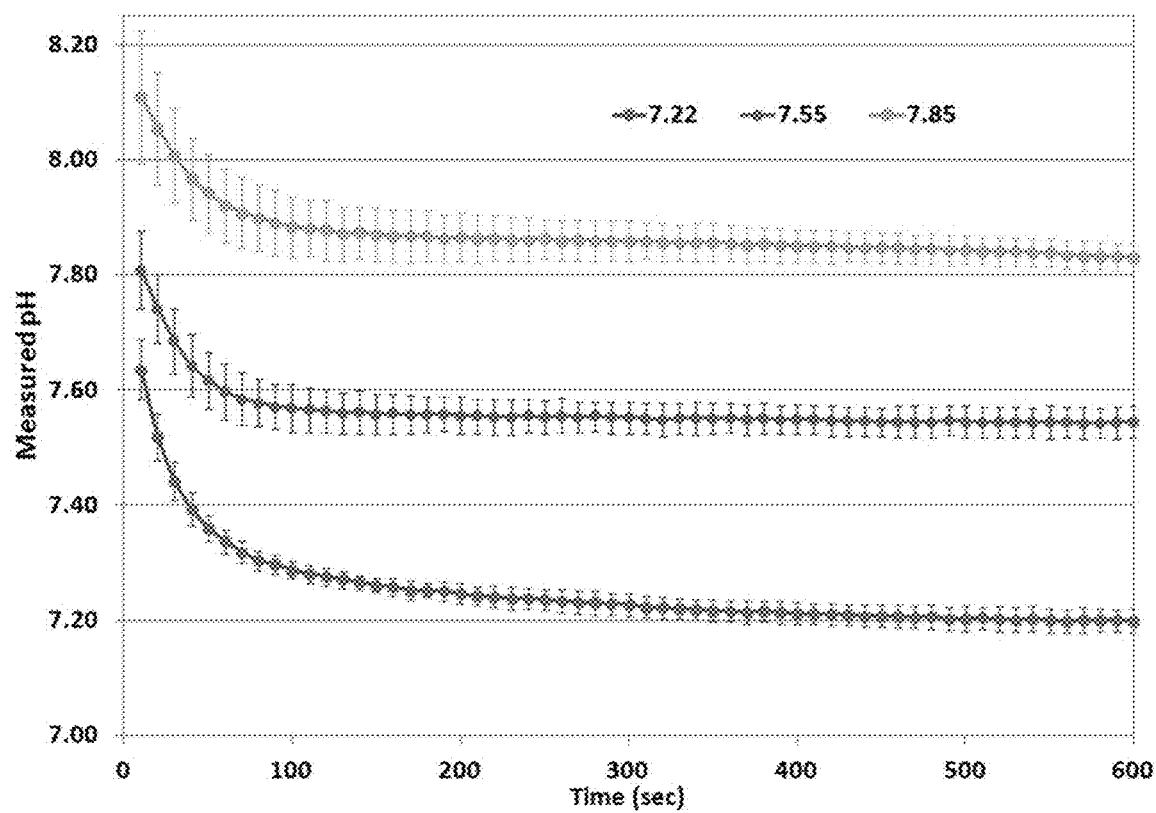
FIG. 9 is a representative graph of pH versus time for samples immersed in simulated pool water containing 3 ppm chlorine as a function of pH.

FIG. 9 shows a representative graph of pH as a function of time for samples immersed in pool water containing 3 ppm free chlorine at various pH. The initial pH of the paper is determined by the manufacturing operations. In FIG. 9, the pH of the paper at the completion of manufacturing is approximately 8. A characteristic of covalently binding the dye to the paper is that it takes over 100 seconds to approach the actual pH of the test solution due to the buffering aspects of the covalently bonded dye starting at a higher pH than the test water and the low buffering capacity of pool water or simulated pool water. The covalently bonded dyes did not desorb as is witnessed for adsorbed test products. This allows the pH paper to be immersed in water for long times without affecting the spectral properties of the paper, unlike most commercial products manufactured for home pool water pH determinations.

What is claimed is:

1. A composition comprising (a) a methylol derivative of a sulfonephthalein dye compound and (b) an oligomer of the sulfonephthalein dye compound.

2. The composition of claim 1, wherein the sulfonephthalein dye is selected from the group consisting of phenol red, cresol red, m-cresol purple, xylenol blue, thymol blue, chlorophenol red, bromophenol blue, bromocresol purple, bromocresol green, bromothymol blue, xylenol orange, and methylthymol blue.

3. The composition of of claim 1 wherein the methylol derivative of the sulfonephthalein dye is selected from compounds represented by Formula (I)

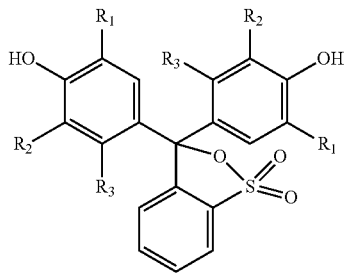

(I)

wherein $R_1$, $R_2$ and $R_3$ for each compound are set forth in Table 2,

TABLE 2

| Compound | $R_1$ | $R_2$ | $R_3$ |
|---|---|---|---|
| 1 | $HOCH_2-$ | H | H |
| 2 | Me | $HOCH_2-$ | H |
| 3 | $HOCH_2-$ | H | Me |
| 4 | H | $HOCH_2-$ | Me |
| 5 | Me | $HOCH_2-$ | Me |
| 6 | i-Pr | $HOCH_2-$ | Me |
| 7 | Cl | $HOCH_2-$ | H |
| 8 | $CH_2N(CH_2COOH)_2$ | $HOCH_2-$ | Me. |

* * * * *